United States Patent [19]

Hampar et al.

[11] Patent Number: 4,572,896

[45] Date of Patent: Feb. 25, 1986

[54] MONOCLONAL ANTIBODIES TO HERPES SIMPLEX VIRUS TYPE I POLYPEPTIDES

[75] Inventors: Berge Hampar, Middletown; Martin Zweig, Walkersville; Stephen D. Showalter, Gaithersburg, all of Md.

[73] Assignee: The United States of America as represented by the Department of Health and Human Services, Washington, D.C.

[21] Appl. No.: 443,682

[22] Filed: Nov. 22, 1982

Related U.S. Application Data

[63] Continuation-in-part of Ser. No. 181,954, Aug. 27, 1980, Pat. No. 4,430,437.

[51] Int. Cl.⁴ ............... C12P 21/00; C12N 15/00; G01N 33/54
[52] U.S. Cl. ..................... 435/172.2; 260/112 R; 435/68; 435/240; 435/948; 436/511; 436/548; 935/103; 935/106; 935/110
[58] Field of Search ............. 435/68, 240, 948, 172.2; 935/103, 106, 110; 260/112 R; 436/511, 548

[56] References Cited

U.S. PATENT DOCUMENTS 4,391,911 7/1983 Tarro .................................. 435/68 X

OTHER PUBLICATIONS

Showalter, S. D. et al., Infection and Immunity, 34(3), 684-692 (Dec. 1981).
Nowinski, R. C. et al., Virology, 93, 111-126 (1979).
Martinis, J. et al., Proc. Natl. Acad. Sci., USA, 75(5), 2320-2323 (May 1978).
Kohler, G. et al., Eur. J. Immunol., 6, 511-519 (1976).
Kohler, G. et al., Nature, 256, 495-497 (Aug. 7, 1975).
Zweig, M. et al., Journal of Virology, 35, 644-652 (Sep. 1980).
Zweig, M. et al., Journal of Virology, 32(1), 676-678 (Nov. 1979).
Zweig, M. et al., Virology, 94, 442-450 (1979).
Heilman, Jr., C. J. et al., Journal of Virology, 29, 34-42 (Jan. 1979).

Primary Examiner—Sidney Marantz
Attorney, Agent, or Firm—John S. Roberts, Jr.

[57] ABSTRACT

A method for producing monoclonal antibody reagents against novel proteins induced by herpes simplex virus type 1 (HSV-1). The method consists of preparing HSV-1 antigen populations by infecting mammalian cells either with HSV-1 alone or with HSV-1 in the presence of an inhibitor of protein synthesis, allowing virus replication to proceed by reversing the action of said inhibitor, inoculating said antigen mixture in mice to induce the production of antibodies, fusing the spleen cells of said mice with myeloma cells to obtain hybrid cells, and screening said cells by radioimmunoprecipitation-polyacrylamide gel electrophoresis (RIP-PAGE) to identify hybrid cells producing monoclonal antibodies against HSV-1 proteins. The method teaches the production of unique monoclonal antibody reagents directed against novel HSV-1 proteins; including a 132,000 molecular weight (mw) DNA-binding protein, a 175,000 mw immediate-early protein, and a previously unknown 110,000 mw glycoprotein.

13 Claims, 1 Drawing Figure

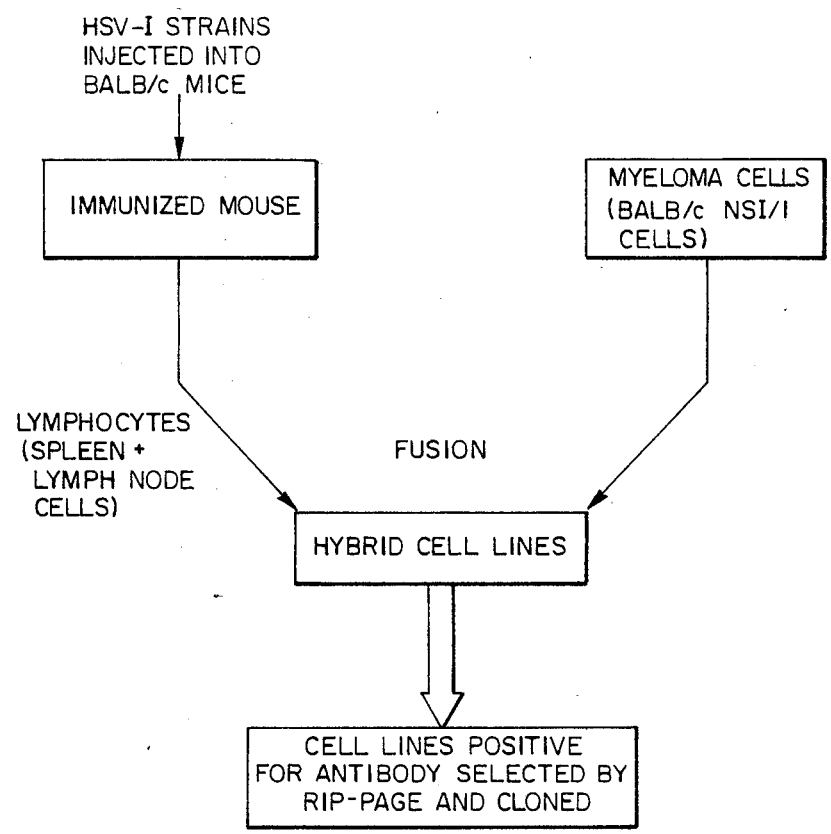

MONOCLONAL ANTIBODIES TO HERPES SIMPLEX VIRUS TYPE I POLYPEPTIDES

The present application is a continuation-in-part application of Ser. No. 181,954 filed Aug. 27, 1980 now U.S. Pat. No. 4,430,437. The parent application teaches a process for developing and employing monoclonal antibodies made against a 40,000 MW protein of herpes simplex virus (HSV) types I (HSV-I) and II (HSV-II), said antibodies being useful for differentiating HSV-I and HSV-II. The present application teaches a process for developing monoclonal antibodies against a variety of HSV-I proteins in a fashion whereby the specificity of the antibodies can be determined immediately. The process is equally applicable for developing monoclonal antibodies against HSV-II proteins.

Previously described techniques for developing monoclonal antibodies against HSV-I and HSV-II proteins employed immunologic techniques for screening hybrid cells for antibody production which did not identify the specific protein of HSV-I or HSV-II against which the antibody was directed. These techniques included, interalia, immunofluorescence (Balachandran et al., *J. Virol.* 39:438–446, 1981; Pereria et al., *Inf. & Immun.*, 35:363–367, 1982); enzyme-linked immunoassay (ELISA) (Balachandra et al., supra); virus neutralization (Pereira et al., supra); immunodiffusion (Zweig et al., *J. Virol.*, 32:676–678, 1979); and $^{125}$I-protein A assay (Killington et al., *J. Virol. Methods*, 2:223–236, 1981). While each of these procedures was effective in identifying hybrid cells releasing antibodies reactive with HSV-I antigens, none was designed to identify the specific protein against which the antibody was directed.

The compounds and composition of the present invention show activity and utility by standard antiviral and biochemical tests in animals (mice) and in tissue to positively show selection of HSV-I.

The present application teaches a method for developing monoclonal antibodies against HSV-I proteins whereby the protein against which the antibody is directed can be identified immediately. The subject method also allows for the immediate identification of antibodies capable of precipitating specific HSV-I proteins as well as identifying antibodies which react type-specifically with HSV-I proteins or cross-react with HSV-II proteins.

A detailed description of the method of the present application was published in Showalter et al., *Infection & Immunity*, 34:684–692, 1981, and is included in the present application by reference. Using this method, a total of fifty-two (52) monoclonal antibodies were isolated against ten (10) HSV-I proteins. Included were two (2) monoclonal antibodies (52S and 53S) against a previously unknown HSV-I glycoprotein, one (1) monoclonal antibody (39S) against ICP-8, a 132,000 MW DNA-binding protein of HSV-I, and one (1) monoclonal antibody (58S) against ICP-4, an immediate-early protein of HSV-I.

UTILITY STATEMENT

The process of the present application is useful for isolating monoclonal antibodies against HSV-I proteins in mice and identifying the protein against which the antibody is directed. The monoclonal antibodies developed using the subject process are useful for identifying a previously unknown 110,000 MW glycoprotein of HSV-I and for identifying ICP-8, a 132,000 MW DNA-binding protein of HSV-I, and ICP-4, a 175,000 MW immediate-early protein of HSV-I. The monoclonal antibodies of this invention are useful in the clinical diagnosis of HSV-I infection in humans and animals wherein cells from clinical lesions can be tested by immunofluorescent or immunoperoxidase techniques for reactivity with said monoclonal antibodies.

PRIOR ART STATEMENT

Heilman et al., J. Virol., 29:34–42, 1979.
Zweig et al., Virology, 94:442–450, 1979.
Zweig, et al., J. Virol., 32-676–678, 1979.
Zweig et al., J. Virol., 35-644–652, 1980.
Kohler, et al., Nature (London), 256:495–496, 1975.
Kohler, et al., Eur. J. Immunol., 6:511–519, 1976.
Koprowski, et al., Proc. Natl. Acad. Sci. USA, 74:2985–2988, 1977.
Martinis, et al., Proc. Natl. Acad. Sci. USA, 75:2320–2323, 1978.
Nowinski, et al., Virology, 93:111–126, 1979.
Showalter, et al., Infection & Immunity, Vol. 34, No. 3, December 1981, pp. 684–692.

STATEMENT OF DEPOSIT

The following monoclonal antibodies have been deposited at the ATCC with the designated numbers as indicated:

| | |
|---|---|
| 39-S | ATCC No. HB 8180 |
| 52-S | ATCC No. HB 8181 |
| 53-S | ATCC No. HB 8182 |
| 58-S | ATCC No. HB 8183 |

In accordance with the Budapest Treaty and current U.S. practice, duration of the deposit is for 30 years from date of deposit or for five years after the last request for deposit at the depository or for the enforceable life of the U.S. patent, whichever is longer.

DESCRIPTION OF THE FIGURE

The FIGURE in a RIP-PAGE of radioimmunoprecipitates from HSV-I infected cell extracts labeled with $^{35}$S-methionine and reacted with monoclonal antibodies, unclassified glycoprotein of 110,000 MW (Lane A), ICP 8 (Lane B), ICP 4 (Lane C, cyclohexamide-treated cells).

BACKGROUND AND GENERAL DESCRIPTION

It is now possible to make pure antibodies to proteins by application of the "monoclonal antibody" or "hybridoma" technique. The present invention is one such new technique which embodies the monoclonal antibody mechanism. About 50 proteins have been discovered of herpes simplex viruses type I and II; the present invention teaches the development of four monoclonal antibodies specific for particular proteins of HSV-I. The accompanying diagram illustrates the general process: it should be noted that this process applies to each monoclonal antibody developed, and that each monoclonal antibody specifies one particular protein. For example, the monoclonal antibodies of this invention immunoprecipitate proteins with molecular weights of 110,000, 132,000, and 175,000. The 110,000 MW protein is a newly discovered HSV-I glycoprotein, whose existence has only recently been noted in *Infection and Immunity*, pp. 684–692, 1981.

Conjugated proteins are those yielding not only amino acids but also other inorganic or organic components. The non-amino acid portion of a conjugated protein is called the "prosthetic group," and is classified according to the chemical nature of the prosthetic group. For example, nucleo-proteins contain nucleic acids as a prosthetic group; the glycoproteins of the present invention may contain hexosamine, galactose, mannose, or sialic acid. Proteins exhibit a variety of biological functions and are classified according to that function. For example, the largest group of proteins are enzymes; other proteins store nutrients for growing embryos or exhibit a transport function. The present invention is concerned with proteins that exhibit a protective or defensive function. These proteins are antibodies, or immune globulins, which combine with and thus neutralize foreign proteins and other substances that gain entrance into the blood or tissues of a vertebrate. In addition, due to the mechanism for combining and neutralizing foreign proteins, antibodies are diagnostic tools used to determine the identity of foreign matter such as viruses. Antibody molecules appear in the blood serum of a vertebrate in response to the introduction of a protein or some other macromolecule foreign to that species; such a species-foreign macromolecule is called the "antigen." The specific antibody molecules generated in this manner combine with the antigen which elicited their formation to form an antigen-antibody complex. Most importantly, these antibody molecules contain binding sites that are specific for and complementary to the structural features or epitopes of the antigen. Again referring to the diagram, the fusion of the lymphocytes and the myeloma cells form hybrid cell lines which elicit the formation of antibodies specific for certain proteins of either HSV-I or HSV-II. By using a radioimmunoprecipitation-SDS-gel detection technique (RIP-PAGE), hybrid cells producing monoclonal antibodies as well as the specific HSV-I protein against which the antibodies are directed can be identified in one step.

DESCRIPTION OF THE MONOCLONAL ANTIBODIES

A total of 52 monoclonal antibodies was prepared against 10 HSV-I proteins. These antibodies were classified into groups based on their properties. The properties used for classification included SDS-polyacrylamide gel electrophoresis of radioimmunoprecipitates (RIP-PAGE), immunofluorescence, and neutralization. Antibodies were further classified as to their type-specificity for HSV-I or cross-reactivity with HSV-II.

The designation of the protein(s) precipitated by each antibody was, according to classification, proposed by Spear (J. Virol., Vol., 17, pp. 991-1008, 1976), Honess and Roizman (J. Virol., Vol. 12 pp. 1347-1365, 1973), and is based on the apparent MW observed by RIP-PAGE. Antibodies which precipitated proteins that could be labeled with either $^{35}$S-methionine or $^3$H-mannose were classified as being directed against glycosylated proteins, while those which precipitated proteins that could only be labeled with $^{35}$S-methionine were classified as being directed against nonglycosylated proteins.

110,00 MW Glycoprotein

Four monoclonal antibodies were prepared against a previously unclassified glycoprotein which precipitates proteins that migrate in SDS gels as a closely spaced band doublet at an apparent MW of 110,000 (the FIGURE, Lane A). We seek patent protection for two of these antibodies. Antibody 53S (Ig type G2a) cross-reacts with HSV-II by RIP-PAGE and immunofluorescence but only neutralizes HSV-I. Antibody 52S (Ig type G2a) reacts type-specifically with HSV-I by RIP-PAGE, immunofluorescence and neutralization.

Convincing evidence that the 110,000 MW glycoprotein precipitated by monoclonal antibodies 52S and 53S differs from the 120,000 MW glycoprotein gA/gB was obtained by showing that the peptide maps of the two glycoproteins were distinct and that neither protein could remove antibody activity to the other. Another distinction between these two glycoproteins is that gA/gB shows partial degradation in mouse and Vero cells but not in human HEp-2 cells, while the band patterns in SDS-gels for the 110,000 MW glycoprotein are identical in these three cell lines.

132,000 MW Non-glycosylated ICP 8

One monoclonal antibody, designated 39S (Ig type G2a), was prepared against HSV-I ICP 8 which immunoprecipitates a DNA-binding protein which migrates in SDS-gels at an apparent MW of 132,000 (the FIGURE, Lane B). Antibody 39S reacts type-specifically with HSV-I by RIP-PAGE and immunofluorescence but does not neutralize HSV-I (see the Table below).

175,000 MW Non-glycosylated ICP 4

One monoclonal antibody, designated 58S, was prepared against the HSV-I immediate early protein ICP 4 which migrates in SDS-gels at an apparent MW of 175,000 (the FIGURE, Lane C). Antibody 58S (Ig type G2a) reacts type specifically with HSV-I by RIP-PAGE and nuclear immunofluorescence but does not neutralize HSV-I.

SPECIFIC DESCRIPTION OF THE INVENTION

Two procedures were used for the immunization of BALB/c mice: Procedure A utilized infectious virus propagated in mouse cells, and Procedure B utilized mouse cells infected with herpes simplex virus in the presence of cycloheximide and harvested one hour after removal of the inhibitor. Monoclonal antibody synthesizing 39S was prepared using Procedure A; monoclonal antibodies synthesizing 52S, 53S, 58S were prepared using Procedure B.

Procedure A

HSV type I (strain 14012) was propagated in mouse 10E2 cells and assayed in Vero cells. The infected cells were pelleted, resuspended in phosphate buffered saline (PBS) and sonicated. The virus suspension was clarified and 0.5 ml (titering $10^8$ plaque-forming units per ml in Vero cells) was inoculated subcutaneously at 7-day intervals over a 14-day period in 8-week-old BALB/c mice. Serum samples were obtained by orbital bleeding for testing antibody production by RIP-PAGE. Three days after the last immunization, animals showing a good antibody response were sacrificed and their spleens were removed for hybridization.

Procedure B

Mouse 10E2 cells were infected with strain 14012 at a multiplicity of infection (MOI) of 20 (determined by virus titration in Vero cells) in the presence of cyclohexamide (50 ug/ml). The infected cells were incubated on a rocker platform at 36° C. for 5 hours, washed 5 times, re-fed with growth medium (Eagle's minimal essential medium containing 10% heat-inactivated fetal calf serum), incubated for one hour, dislodged by trypsin-EDTA, pelleted, resuspended in PBS ($6 \times 10^7$ cells in 1.5 ml PBS) and sonicated. The cell suspension was clarified and the supernatant was mixed with an equal volume of Freund's complete adjuvant for intraperitoneal inoculation of BALB/c mice. The procedure was repeated after 7 days using incomplete adjuvant and subcutaneous inoculation. The final subcutaneous inoculation without adjuvant was given after an additional 7 days. Spleens were harvested three days later from antibody-producing animals.

The procedure for fusing mouse spleen cells with mouse myeloma was a modification of that we previously described (Zweig, et al., J. Virol., 32:676–678, 1979). Spleens removed from virus-immunized mice were minced, passed through sterile gauze, placed in a 50 ml conical centrifuge tube, and washed 3 times in cold, serum-free medium by centrifugation at $200 \times g$ for 5 minutes. The spleen cells were counted and mixed with actively growing NS1/1 cells at 5:1 ratio. Cell mixtures were pelleted at $200 \times g$ for 5 minutes and were gently resuspended during a one-minute period in 1 ml of 50% polyethylene glycol (PEG-1500) per $1.6 \times 10^8$ lymphocytes. After two minutes, 2 ml of RPMI-1640 containing 15% fetal calf serum was added dropwise with gentle mixing over a period of two minutes. At five minutes after the addition of the PEG, 10 ml of additional medium was added rapidly and the cells were pelleted at $200 \times g$ for five minutes. The supernatant fluids were aspirated, the pellets resuspended very gently in 22 ml of medium, and the cells aliquoted (approximately 100 ul per well) into 96-well tissue culture plates. After 24 hours, 100 ul RPMI-1640 with 15% fetal calf serum containing hypoxanthine-aminopterine-thymidine (HAT) was added. On days 2, 3, 4, 7 and 10 following hybridization, approximately 100 ul medium was removed from each cell, and was replaced with 100 ul HAT-containing medium. On day 14, and at 3-4 day intervals thereafter until one month following hybridization, the cells were re-fed with medium containing hypoxanthine-thymidine (HT). Thereafter, cells were maintained in medium with HT. Beginning about day 10, the clarified medium from wells showing cell growth was tested by RIP-PAGE for antibody activity. The cells from positive wells were transferred to 24-well plates and were cloned by limiting dilution in 96-well plates with feeder layers of compatible thymocytes.

Clones producing desired antibodies were passaged in ascites form by intraperitoneal injection of $2-5 \times 10^6$ cells into BALB/c mice primed two weeks previously with 0.5 ml of pristane (2,6,10,14 tetramethylpentadecane) which had been injected intraperitoneally. The resulting fluids were harvested, clarified, and tested.

Screening for monoclonal antibodies was by SDS-polyacrylamide gel electrophoresis of radioimmunoprecipitates (RIP-PAGE). 10E2, Vero or HEp-2 cells were infected with HSV-I (strains 14012, Miyama, MP or MAL) or HSV-II (strains 333, MS dor Savage) at a MOI of 5. Following incubation for one hour at 37°, the inocula were removed, and the cells were radiolabeled for 8 hours with either 100 uCi of $^{35}$S-methionine (800–1,200 Ci/mmol) per ml in methionine-free Eagle's minimal essential medium containing 5% dialized heat-inactivated fetal calf serum or 50 Ci of D-[2-$^3$H] mannose (16 Ci/mmol) per ml in Eagle's minimal essential medium containing 20% the normal concentration of glucose and 5% heat-inactivated fetal calf serum. The cell monolayers were washed 3 times with cold Tris-buffered saline (pH 7.2) and were then mixed for one hour at 4° C. in extraction buffer(0.1M Tris-hydrochloride [pH 8.0], 10% (vol/vol) glycerol, 0.5% Nonidet P-40, 0.5% sodium deoxycholate, 0.2 mN phenylmethylsulfonyl fluoride. After clarification by centrifugation at $60,000 \times g$ for one hour, the extracts were incubated with ascites fluids and subsequently with protein A-Sepharose CL-4B. The immunoprecipitated proteins were separated by electrophoresis on a 5–20% polyacrylamide gradient containing SDS and autoradiographs or fluorographs were prepared on Kodak SB-5 X-ray film.

To test antibody activity against immediate early (OC) proteins, cells were infected at a MOI of 20 in the presence of 50 ug ml$^{-1}$ cycloheximide. After incubation for five hours, the cells were washed five times, refed with medium, incubated one hour, and labeled as above for one hour.

The immunoglobulin class and subclasses were determined by double-diffusion using agar gel plates and rabbit antisera to specific mouse immunoglobulins. Test samples (8 ul) and typing reagents (8 ul) were added to adjacent wells and allowed to diffuse overnight at room temperature in a humidified chamber.

Ascites fluids were tested for neutralizing activity against HSV-I (strain 14012) and HSV-II (strain 333). The reaction mixtures containing 0.5 ml virus ($10^3$ pfu) plus 0.5 ml diluted ascites fluid plus 40 ul fresh or heat-inactivated guinea pig complement (C) were placed at 34° C. for 30 minutes. Fresh medium was added to bring the volume to 10 ml, and 1 ml aliquots were inoculated on Vero cell monolayers in 60 mm petri dishes. The infected cells were incubated for two hours at 37° C. The inocula were removed and replaced with medium containing methyl-cellulose. After 3–4 days, the cells were fixed, stained and plaques counted. The antibody titer was determined as that dilution of ascites fluid which reduced plaque numbers by 50% or more.

Human W1-38 cells, primate Vero cells or mouse 10E2 cells grown on coverslips were infected with either HSV-I (strain 14012) or HSV-II (strain 333) at a MOI of 0.001 to 10. After 24–48 hours, when discreet plaques were evident, the coverslips were washed in PBS, the cells were air-dried at room temperature, fixed for 3–4 minutes in acetone and dried at room temperature. Ascites fluids diluted in PBS were added to the cells which were then placed in a humidified chamber of room temperature for 45 minutes. After the cells were washed several times in PBS, fluorescein isothiocyanate-conjugated goat anti-mouse immunoglobulin was added, and the cells were incubated in a humidified chamber for 45 minutes. The cells were washed in PBS, counterstained with Evans blue, and mounted on slides with elvanol for uv-microscopy. Antibodies were also tested for reactivity with HSV infected human or animal cells by standard immunoperoxidase techniques. The results by immunoperoxidase were essentially similar to those obtained by immunofluorescence.

| MW | Monoclonal Antibody | Immunoglobulin Type | RIP-PAGE (HSV-I/HSV-II) | FA* (Acetone Fixed) HSV-I | HSV-II | Neutralization No Complement HSV-I | HSV-II | Complement HSV-I | HSV-II |
| --- | --- | --- | --- | --- | --- | --- | --- | --- | --- |
| 110,000 | 53S | Ig2a | +/+ | 5,120 | 2,560 | 200 | <25 | 200 | <25 |
| 110,000 | 52S | Ig2a | +/− | 640 | <20 | 800 | <25 | 800 | <25 |
| 132,000 | 39S | Ig2a | +/− | 640 | <20 | <25 | <25 | <25 | <25 |
| 175,000 | 58S | Ig2a | +/− | 320 | <20 | <25 | <25 | <25 | <25 |

*Results equally applicable for humans, primate and mouse cells infected with HSV.

We claim:

1. A method for isolating monoclonal antibodies to specific HSV-1 proteins consisting essentially of fusing lymphoid cells from mice infected with HSV-I infected cell extracts to myeloma cells, selecting for the resulting hybrid cells in hypoxanthine-aminopterin-thymidine (HAT) medium, and analyzing the fluids from hybrid cell cultures by SDS-polyacrylamide gel electrophoresis of radioimmunoprecipitates (RIP-PAGE) formed with $^{35}$S-methionine labelled HSV-1 infected cell extracts.

2. The method in claim 1 wherein the monoclonal antibodies are prepared against immediate-early proteins of HSV-1 using cycloheximide-treated cells infected with HSV-1 for immunization of mice and detection of antibodies by RIP-PAGE.

3. The method of claim 1 wherein the monoclonal antibody is designated 52S, said monoclonal antibody having the essential characteristics of ATCC. No. HB8181, said characteristics include specificity for HSV-1 glycoprotein of 110,000 mw by RIP-PAGE, immunofluorescence and neutralization.

4. The method of claim 3 wherein the monoclonal antibody is designated 53S, said monoclonal antibody having the essential characteristics of ATCC No. HB8182, said characteristics include cross-reactivity with an HSV-II glycoprotein by RIP-PAGE and immunofluorescence.

5. The method of claim 1 wherein the monoclonal antibody is designated 39S, said monoclonal antibody having the essential characteristics of ATCC. No. HB8180, said characteristics include specificity for an HSV-I DNA-binding protein of 132,000 mw by RIP-PAGE and immunofluorescence.

6. The method in claim 2 wherein the monoclonal antibody is designated 58S, said monoclonal antibody having the essential characteristics of ATCC. No. HB8183, said characteristics include specificity for an HSV-I immediate-early protein of 175,000 MW of RIP-PAGE and immunofluorescence.

7. A method for isolating monoclonal antibodies to specific HSV-1 proteins consisting essentially of fusing lymphoid cells from mice infected with HSV-1 infected cell extracts to myeloma cells to form hybrid cells; screening RIP-PAGE analysis said hybrid cells that are positive for said antibody and cloning the positive hybrid cells.

8. A method for producing monoclonal antibodies to proteins induced by HSV-1 consisting essentially of infecting mammalian cells with HSV-1 virus and allowing HSV-1 virus replication to proceed, harvesting said infected cells and inoculating said infected cells into mice, fusing spleen cells from said mice to myeloma cells to produce hybrid cells, screening said hybrid cells by radioimmunoprecipitation-polyacrylamide gel electrophoresis (RIP-PAGE) against isotope-labeled virus-infected cells to identify cells producing monoclonal antibodies directed against HSV-1 proteins, and isolating said monoclonal antibody-producing hybrid cells in order to prepare ascites fluids containing said antibody.

9. The method of claim 8 for preparing a monoclonal antibody, designated 52S, which is specific for HSV-1 by RIP-PAGE, immunofluorescence and neutralization, and is directed against a HSV-1 glycoprotein of 110,000 mw.

10. The method of claim 8 for preparing a monoclonal antibody, designated 39S, which is specific for HSV-1 by RIP-PAGE and immunofluorescence, and is directed against a HSV-1 DNA-binding protein of 132,000 mw.

11. A method for producing monoclonal antibodies to proteins induced by HSV-1 consisting essentially of infecting mammalian cells with HSV-1 in the presence of cycloheximide, removing said cycloheximide after five hours, incubating the cycloheximide-free cells for one hour, harvesting and inoculating said infected cells into mice, fusing spleen cells from said mice to myeloma cells to produce hybrid cells, screening said hybrid cells by RIP-PAGE against isotope-labelled cycloheximide-treated virus infected cells to identify cells producing monoclonal antibodies directed against HSV-1 proteins, and isolating said monoclonal antibody-producing hybrid cells and using said hybrid cells to prepare ascites fluids containing said antibody.

12. The method of claim 11 for preparing a monoclonal antibody, designated 58S, which is specific for HSV-1 by RIP-PAGE and immunofluorescence, and is directed against an HSV-1 immediate-early protein of 175,000 mw.

13. The method of claim 11 for preparing a monoclonal antibody, designated 53S, which is directed against a HSV-1 glycoprotein of 110,000 mw and is specific for HSV-1 by neutralization, and which cross-reacts with an HSV-2 110,000 mw glycoprotein by RIP-PAGE and immunofluorescence.

* * * * *

UNITED STATES PATENT OFFICE
CERTIFICATE OF CORRECTION

Patent No. 4,572,896        Dated February 25, 1986

Inventor(s) Berge Hampar, Martin Zweig and Stephen D. Showalter

It is certified that error appears in the above-identified patent and that said Letters Patent are hereby corrected as shown below:

Col. 7, claim 6, line 5, change "MW" to --mw--.

claim 7, line 5, after "screening" insert

--by--.

Signed and Sealed this

Twenty-third Day of September 1986

[SEAL]

Attest:

DONALD J. QUIGG

Attesting Officer        Commissioner of Patents and Trademarks